(12) United States Patent
Whitman et al.

(10) Patent No.: US 9,670,454 B2
(45) Date of Patent: Jun. 6, 2017

(54) METHODS OF MICROALGAE CULTIVATION FOR INCREASED RESOURCE PRODUCTION

(71) Applicant: ENTECH, LLC, Hermiston, OR (US)

(72) Inventors: John Whitman, Hermiston, OR (US); Robert G. Barton, Hermiston, OR (US); Michael Ripka, III, Lakewood, WA (US); Michael Ripka, Jr., Lakewood, WA (US); Robert L. Harris, Las Vegas, NV (US)

(73) Assignee: Entech, LLC, Hermiston, OR (US)

( * ) Notice: Subject to any disclaimer, the term of this patent is extended or adjusted under 35 U.S.C. 154(b) by 0 days.

(21) Appl. No.: 15/231,600

(22) Filed: Aug. 8, 2016

(65) Prior Publication Data

US 2016/0348062 A1    Dec. 1, 2016

Related U.S. Application Data

(62) Division of application No. 14/701,309, filed on Apr. 30, 2015, now Pat. No. 9,441,197.

(60) Provisional application No. 61/987,695, filed on May 2, 2014.

(51) Int. Cl.
　　*C12P 21/00*　　(2006.01)
　　*C12N 1/12*　　(2006.01)
　　*C12P 7/64*　　(2006.01)

(52) U.S. Cl.
　　CPC ............. *C12N 1/12* (2013.01); *C12P 7/6409* (2013.01); *C12P 7/6463* (2013.01); *C12P 21/00* (2013.01)

(58) Field of Classification Search
　　None
　　See application file for complete search history.

(56) References Cited

U.S. PATENT DOCUMENTS

2012/0149075 A1*　6/2012　Day ................ C12P 7/6418
　　　　　　　　　　　　　　　　　　　　　　　　　　　　435/134
2013/0295268 A1　11/2013　Day et al.
2015/0315538 A1　11/2015　Whitman et al.

FOREIGN PATENT DOCUMENTS

EP　　　2292782　　*　9/2011　............ C12P 7/64
WO　　2008/151149　　　12/2008

OTHER PUBLICATIONS

Bumbak et al., Best practices in heterotrophic high-cell-density microalgal processes: achievements, potential and possible limitations, Appl. Microbiol. Biotechnol (2011) 91:31-46.*

(Continued)

*Primary Examiner* — Suzanne M Noakes
*Assistant Examiner* — Stephen Chong
(74) *Attorney, Agent, or Firm* — Stoel Rives LLP; Zhi-Xiang (Alex) Oh

(57) ABSTRACT

Methods of inducing or increasing lipid and protein production in microalgae are disclosed. Methods of enhancing microalgae biomass are also disclosed. The methods may comprise inoculating a culture media with microalgae and propagating the microalgae under heterotrophic growth conditions. The heterotrophic growth conditions may comprise inhibiting exposure of the inoculated culture media to light. The methods may further comprise delivering oxygen into the inoculated culture media. Additionally, lipids, proteins, and other cellular components may be isolated and purified from microalgae cultivated under the disclosed methods.

22 Claims, 8 Drawing Sheets

(56) References Cited

OTHER PUBLICATIONS

Chi et al., Study of a two-stage growth of DHA-producing marine algae Schizochytrium limacinum SR21 with shifting dissolved oxygen level, Appl. Microbiol Biotechnol (2009) 81: 1141-1148.*

Frenz, et al, "Hydrocarbon recovery by extraction with a biocompatible solvent from free and immobilized cultures of Botryococcus braunii," Enzyme Microb. Technol., vol. 11, pp. 717-724, (Nov. 1989).

Hejazi, et al., "Mechanism of Extraction of β-Carotene from Microalga Dunaliella salina in Two-Phase Bioreactors," Biotechnology and Bioengineering, vol. 88, No. 5, pp. 593-600, (Dec. 5, 2004).

Hejazi, et al., "Milking Microalga Dunaliella salina for β-Carotene Production in Two-Phase Bioreactors," Biotechnology and Bioengineering, vol. 85, No. 5, pp. 475-481, (Mar. 5, 2004).

Inoue, et al., "Analysis of Oil Derived From Liquefaction of Botryococcus Braunii," Biomass and Bioenergy, vol. 6, No. 4, pp. 269-274, (1994).

International Search Report and Written Opinion issued Aug. 5, 2015 in International Application No. PCT/US2015/28618.

Mendes, et al., "Supercritical carbon dioxide extraction of compounds with pharmaceutical importance from microalgae," Inorganica Chimica Acta, vol. 356, pp. 328-334, (2003).

Miao, et al., "Biodiesel production from heterotrophic microalgal oil," Bioresource Technology, vol. 97, pp. 841-846, (2006).

Miao, et al., "High yield bio-oil production from fast pyrolysis by metabolic controlling of Chlorella protothecoides," Journal of Biotechnology, vol. 110, pp. 85-93, (2004).

Minowa, et al., "Oil production from algal cells of Dunaliella tertiolecta by direct thermochernical liquefaction," Fuel, vol. 74, No. 12, pp. 1735-1738, (1995).

Sawayama, et al., "Possibility of renewable energy production and $CO_2$ mitigation by thermochemical liquefaction of microalgae," Biomass and Bioenergy, vol. 17, pp. 33-39, (1999).

U.S. Appl. No. 14/701,309, Apr. 30, 2015, Preliminary Amendment.
U.S. Appl. No. 14/701,309, Jun. 29, 2015, Office Action.
U.S. Appl. No. 14/701,309, Sep. 28, 2015, Response to Office Action.
U.S. Appl. No. 14/701,309, Feb. 2, 2016, Office Action.
U.S. Appl. No. 14/701,309, Apr. 1, 2016, Response to Office Action.
U.S. Appl. No. 14/701,309, May 9, 2016, Notice of Allowance.

\* cited by examiner

Day 1, 0900 hours, 400x

Day 1, 2000 hours, 1000x

Day 2, 0800 hours, 1000x

Day 2, 1000 hours, 1000x

Day 2, 1200 hours, 1000x

Day 3, 0800 hours, 400x

METHODS OF MICROALGAE CULTIVATION FOR INCREASED RESOURCE PRODUCTION

CROSS-REFERENCE TO RELATED APPLICATIONS

This application is a divisional of U.S. application Ser. No. 14/701,309, filed Apr. 30, 2015, which claims the benefit and priority of U.S. Provisional Application No. 61/987,695, filed May 2, 2014. This application hereby incorporates by reference the U.S. application and U.S. provisional application enumerated herein.

TECHNICAL FIELD

The present disclosure relates generally to methods of cultivating microalgae. In particular, the methods may be useful in the increased production of microalgae biomass, protein, and lipid. The present disclosure also relates to microalgae biomass, protein, and lipid isolated and/or purified from microalgae cultivated by one or more of the described methods.

BACKGROUND

Historically, the energy required for the generation of electricity and modern transportation has been largely provided by fossil fuels. Though other energy sources (e.g., wind, solar, hydroelectric, nuclear, etc.) have been developed, used, and are currently available, as a global society, we are still heavily dependent on the combustion of fossil fuels, such as gasoline, diesel fuel, fuel oil, crude oil, coal, and natural gas, to meet our energy and transportation needs. However, with global modernization, the thirst for energy from fossil fuels has grown dramatically, with some estimating that the global energy demand will double within the next several decades.

Increased demand for energy by the global economy has already placed increasing pressure on the cost of fossil fuels and the hydrocarbon products derived there from. This trend is particularly troubling when one considers that energy production is just one of multiple critical uses of hydrocarbons. In particular, many industries, including those based on the production or use of composites, plastics, and manufactured chemicals, rely heavily on the availability of hydrocarbons as a feedstock for their processes and products. Therefore, cost-effective alternatives to fossil fuels as an energy and fuel source would not only help provide for the world's increasing demand for energy, but could also help mitigate the upward cost pressure recently experienced with products produced from fossil fuels.

Energy derived from biomass presents a means of both potentially reducing greenhouse gas emissions and reducing the need for a fossil fuel-based infrastructure, and bioenergy is generally considered to be an important asset in our repertoire of renewable energy solutions. In biological systems, the utilization of energy is accomplished by a cascade of biochemical reactions mediated by tightly regulated metabolic networks.

Microbes such as microalgae show promise as a renewable feedstock for the production of biofuels ranging from ethanol to biodiesel. Algae are a diverse group of aquatic, photosynthetic organisms generally categorized as either macroalgae (i.e., seaweed) or microalgae, which are typically unicellular. Although the field of algal biofuels remains in its infancy, microalgae have great potential to serve as a resource for clean, sustainable fuel production. Algae are effective photosynthetic organisms for generating chemical energy from sunlight, and it is believed that a large percentage of today's fossil fuels, particularly petroleum, originated as prehistoric algal blooms. As single-celled organisms, microalgae are capable of producing a large portion of their biomass as small molecule biofuel precursors since they lack the macromolecular structural and vascular components needed to support and nourish terrestrial plants. As such, algae provide one of the most direct routes for conversion of carbon and other organic substrates to biofuel. Moreover, the large surface area to volume ratio of these aquatic microorganisms is advantageous for absorption of nutrients, which is reflected in the rapid growth rates observed in many species.

Unlike terrestrial bioenergy crops, microalgae do not require fertile land or extensive irrigation and can be harvested continuously. Several species of microalgae do not even require freshwater and may grow in brackish, sea, and even hypersaline water. Additionally, since microalgae consume carbon dioxide ($CO_2$) through the process of photosynthesis, large-scale cultivation may even be used to remediate the $CO_2$ emissions from fossil fuel combustion. Algae biomass also possesses marketable, secondary co-products such as antioxidant pigments, edible proteins, and nutraceutical oils that other alternative fuel crops lack. Nevertheless, hurdles to large-scale commercialization of algal biofuels remain. Among such challenges are: (1) the need to increase algal oil productivity; and (2) the need to improve processing techniques required to access the oil produced by algae.

BRIEF DESCRIPTION OF THE DRAWINGS

The embodiments disclosed herein will become more fully apparent from the following description and appended claims, taken in conjunction with the accompanying drawings.

DETAILED DESCRIPTION

Figure 1:
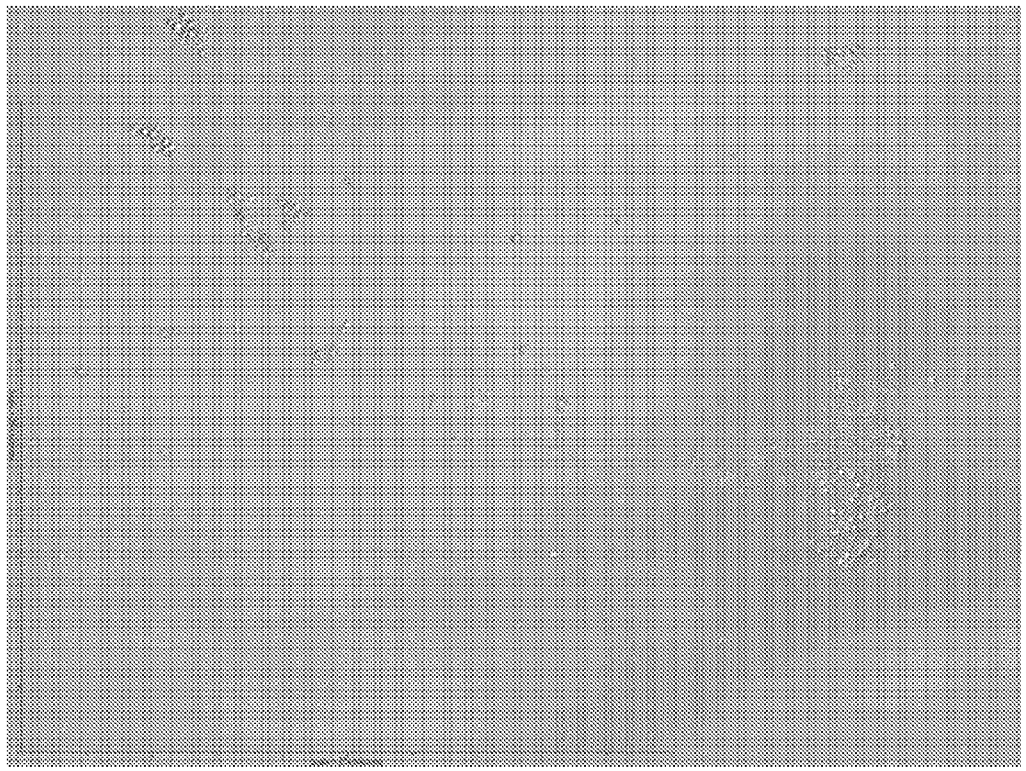
FIG. 1 is a micrograph depicting a sample of microalgae prior to, or at the onset of, being cultivated under heterotrophic growth conditions and with the introduction of oxygen according to an embodiment of the present disclosure. The micrograph was acquired at 0900 hours on day 1 at a magnification of 400×.

Methods of cultivating microalgae are described herein. In particular embodiments, the methods described herein may be useful for providing favorable production of ne or more of the following: microalgae biomass, protein, or lipids. In certain such embodiments, the methods described herein may result in high levels of lipid production from microalgae cultures. Methods according to the present description may be used to produce cultures of microalgae wherein the microalgae cells contain high concentrations of lipid and significant concentrations of lipid are released into the culture media. For example, in certain embodiments, methods described herein may provide microalgae cultures wherein the microalgae accumulate at least 25% of their cell weight as lipid and the fermentation broth includes at least 10% (v/v) lipid. As described herein, methods according to the present description may also be adapted to provide favorable or desired biomass production and/or favorable or desired protein production from microalgal cultures.

Systems for carrying out the methods described herein are also described. Embodiments of such systems may include one or more bioreactors for cultivating microalgae. A bioreactor system suitable for carrying out methods according to the present description may include one or more of the following: one or more bioreactors; one or more fluid, gas, and/or other media sources; circulation lines or conduits for transfer of fluids, gas, culture media, cultured algae, etc.; ports for the ingress or egress of fluids, gas, culture media, cultured algae, etc.; one or more valves for controlling the flow of fluid, gas, and/or other media; one or more pumps; one or more storage tanks; and one or more pressure tanks for containing pressurized fluid, gas, and/or other media. In certain embodiments, the bioreactor systems described herein may include one or more filters for collecting, separating, delivering and/or concentrating the microalgae, the growth media, components of the growth media, one or more process gases, and/or other materials present in or introduced into the bioreactor system.

Various different species of microalgae may be suitable for use in the processes described herein. In some embodiments, a single species of microalgae may be used, but in other embodiments, the cultures used in the methods and processes described herein may include two, three, four, or more species of algae. In further embodiments, the cultures used in the methods and processes described herein may include two, three, four, or more co-cultivated species of algae. The microalgae used may be selected based on one or more of several factors, including, for example, the desired oil yield, the desired protein production, the growth and stability of the microalgae when exposed to process conditions, and the ability of the microalgae to provide reproducible results, and the like. Examples of microalgae species that may be used in the methods described herein include, but are not limited to, freshwater and marine microalgae species such as *Ankistrodesmus, Botryococcus, Cyclotella, Dunaliella, Hantzschia, Nannochloris, Nitzschia, Phaeodactylum, Scenedesmus, Stichococcus, Tetraselmis, Thalassiosira, Crypthecodinium, Neochloris,* or *Schizochytrium* species. In particular embodiments, the microalgae may be a species of the genus *Chlorella*, such as, for example, but not limited to, *Chlorella fusca, C. protothecoides, C. pyrenoidosa, C. kessleri, C. vulgaris, C. saccharophila, C. sorokiniana,* or *C. ellipsoidea*. In certain embodiments, the microalgae may be selected from marine microalgae species such as *Nannochloropsis* species.

Unless otherwise specified, the methods described herein may be carried out using standard materials and equipment that are known to the skilled artisan. For example, solid and liquid growth media are generally available from a wide variety of sources, and instructions for the preparation of particular media that is suitable for a wide variety of strains of microorganisms can be found, for example, online at http://www.utex.org/, a site maintained by the University of Texas at Austin for its culture collection of algae (UTEX). Suitable media for use with the methods described herein can be identified by consulting the URL identified above, or by consulting other organizations that maintain cultures of microorganisms, such as SAG, CCAP, or CCALA. SAG refers to the Culture Collection of Algae at the University of Gottingen (Gottingen, Germany), CCAP refers to the culture collection of algae and protozoa managed by the Scottish Association for Marine Science (Scotland, United Kingdom), and CCALA refers to the culture collection of algal laboratory at the Institute of Botany in the Czech Republic.

Though several methods previously described in the art utilize engineered or genetically modified microalgae to provide increases in lipid yields from microalgae, the methods described herein require no such modifications to the organism itself. As is described herein and is detailed in the examples, utilizing microalgae that are not engineered or genetically modified, embodiments of the methods described herein may quickly achieve high density microalgae cultures with, for example, high lipid content within the cultured microalgae and high concentrations of extracellular lipid in the fermentation broth. In some other embodiments, methods as disclosed herein may utilize engineered or genetically modified microalgae.

It will be readily understood that the embodiments, as generally described herein, are exemplary. The following more detailed description of various embodiments is not intended to limit the scope of the present disclosure, but is merely representative of various embodiments. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified.

Unless specifically defined otherwise, the technical terms, as used herein, have their normal meaning as understood in the art. The following terms are specifically defined with examples for the sake of clarity.

As used herein, the term "biomass" refers to material produced by growth and/or propagation of cells. Biomass may contain cells and/or intracellular contents as well as extracellular material. Extracellular material includes, but is not limited to, compounds (i.e., lipids) secreted by a cell.

As used herein, the term "bioreactor" refers to an enclosure or partial enclosure in which cells are cultured, optionally in suspension. Types of bioreactors include photobioreactors and fermentors. As used herein, the term "fermentor" refers to a bioreactor suited to heterotrophic cultivation and/or propagation of a microalgae culture. The systems for cultivating, propagating, and harvesting algae described herein include at least one bioreactor, and in particular embodiments, systems according to the present description include at least one fermentor.

As used herein, the term "co-culture," and variants thereof such as "co-cultivate," refer to the presence of two or more types or species of algae cells in the same culture or bioreactor.

As used herein, the term "cultivated," and variants thereof, refer to the intentional fostering of growth (i.e., increases in cell size, cellular contents, and/or cellular activity) and/or propagation (i.e., increases in cell numbers via mitosis) of one or more cells by use of intended culture conditions. The combination of both growth and propagation may be termed proliferation. The one or more cells may be those of a microorganism, such as microalgae. Examples of intended conditions include the use of a defined medium (with known characteristics such as pH, ionic strength, carbon source (i.e., type and/or level of carbon source)), specified temperature, oxygen tension or levels, rate of oxygen delivery, carbon dioxide levels, and growth in a bioreactor. The term does not refer to the growth or propagation of microorganisms in nature or otherwise without direct human intervention, such as natural growth of an organism that ultimately becomes fossilized to produce geological crude oil.

As used herein, the term "fixed carbon source" refers to molecule(s) containing carbon present at ambient temperature and pressure in solid or liquid form.

As used herein, the term "hydrocarbon" refers to: (a) a molecule containing only hydrogen and carbon atoms, wherein the carbon atoms are covalently linked to form a linear, branched, cyclic, or partially cyclic backbone to which the hydrogen atoms are attached; or (b) a molecule that only primarily contains hydrogen and carbon atoms and that can be converted to contain only hydrogen and carbon atoms by one to four chemical reactions. Non-limiting examples of the latter include hydrocarbons containing an oxygen atom between one carbon and one hydrogen atom to form an alcohol molecule, as well as aldehydes containing a single oxygen atom. Methods for the reduction of alcohols to hydrocarbons containing only carbon and hydrogen atoms are well known. Another example of a hydrocarbon is an ester, in which an organic group replaces a hydrogen atom (or more than one hydrogen atom) in an oxygen acid. The molecular structure of hydrocarbon compounds varies from the simplest, in the form of methane ($CH_4$), which is a constituent of natural gas, to the very heavy and very complex, such as some molecules such as asphaltenes found in crude oil, petroleum, and bitumens. Hydrocarbons may be in gaseous, liquid, or solid form, or any combination of these forms, and may have one or more double or triple bonds between adjacent carbon atoms in the backbone. Accordingly, the term "hydrocarbon" includes linear, branched, cyclic, or partially cyclic alkanes, alkenes, lipids, and paraffin. Examples include, but are not limited to, propane, butane, pentane, hexane, octane, triolein, and squalene.

As used herein, the term "hydrophobic fraction" refers to the portion, or fraction, of a material that is more soluble in a hydrophobic phase in comparison to an aqueous phase. A hydrophobic fraction is substantially insoluble in water and usually non-polar.

As used herein, the phrase "limiting concentration of a nutrient" refers to a concentration in a culture that limits the propagation of a cultured organism. A "non-limiting concentration of a nutrient" is a concentration that supports maximal propagation during a given culture period. Thus, the number of cells produced during a given culture period is lower in the presence of a limiting concentration of a nutrient than when the nutrient is non-limiting. A nutrient is said to be "in excess" in a culture, when the nutrient is present at a concentration greater than that which supports maximal propagation.

As used herein, the terms "lipid" and "lipids" refer to a class of hydrocarbon that are soluble in nonpolar solvents (such as ether and chloroform) and are relatively or completely insoluble in water. Lipid molecules have these properties because they consist largely of long hydrocarbon tails, which are hydrophobic in nature. Examples of lipids include: fatty acids (saturated and unsaturated); glycerides or glycerolipids (such as monoglycerides, diglycerides, triglycerides, or neutral fats, and phosphoglycerides or glycerophospholipids); nonglycerides (sphingolipids, sterol lipids including cholesterol and steroid hormones, prenol lipids including terpenoids, fatty alcohols, waxes, and polyketides); and complex lipid derivatives (sugar-linked lipids, or glycolipids, and protein-linked lipids). As used herein, the term "fats" refers to a subgroup of lipids referred to as "triacylglycerides."

As used herein, the terms "lysis" and "lysing" refer to disruption of the plasma membrane and, where present, the cell wall of an organism sufficient to release at least some intracellular content. Lysis can be carried out by known mechanical, viral, or osmotic mechanisms that compromise the integrity of the targeted cells. In certain embodiments, lysis of cells is carried out via "cytolysis," which refers to the lysis of cells in a hypotonic environment. Cytolysis is caused by excessive osmosis, or movement of water, towards the inside of a cell (hyperhydration), causing the cell to rupture. As used herein, the term "lysate" refers to a solution, suspension, or dispersion containing the contents of lysed cells.

As used herein, the term "microalgae" refers to a eukaryotic microbial organism that contains a chloroplast, and optionally that is capable of performing photosynthesis, or a prokaryotic microbial organism capable of performing photosynthesis. Microalgae include obligate photoautotrophs, which cannot metabolize a fixed carbon source as energy, as well as heterotrophs, which can live solely off of a fixed carbon source. Microalgae can refer to unicellular organisms that separate from sister cells shortly after cell division, such as *Chlamydomonas*, and can also refer to microbes such as, for example, *Volvox*, which is a simple multicellular photosynthetic microbe of two distinct cell types. The term "microalgae" can also refer to cells such as *Chlorella* and *Dunaliella*. The term "microalgae" can also include other microbial photosynthetic organisms that exhibit cell-cell adhesion, such as *Agmenellum, Anabaena*, and *Pyrobotrys*. The term "microalgae" can also include obligate heterotrophic microorganisms that have lost the ability to perform photosynthesis, such as certain dinoflagellate algae species.

As used herein, the terms "media," "culture media," and "growth media" refer to the materials included with the microalgae in a photobioreactor or fermentor that aid in creating and/or maintaining an environment within which desired microalgal cultures of desired characteristics can be achieved. Such media can be solid or liquid, typically provide one or more nutrients or materials necessary for the desired algal growth, and are generally available from a wide variety of sources. As discussed above, media and instructions for the preparation of media suitable for a wide variety of strains of microalgae can be found, for example, online at http://www.utex.org/, a site maintained by the University of Texas at Austin for its culture collection of algae. Other suitable media for use with the methods of the invention can be readily identified by consulting other organizations that maintain cultures of microorganisms, such as SAG, CCAP, or CCALA. SAG refers to the Culture Collection of Algae at the University of Gottingen (Gottingen, Germany), CCAP refers to the culture collection of algae and protozoa managed by the Scottish Association for Marine Science (Scotland, United Kingdom), and CCALA refers to the culture collection of algal laboratory at the Institute of Botany, Czech Republic.

Heterotrophic Cultivation of Microalgae

The methods described herein may include cultivating a culture of microalgae under heterotrophic growth conditions. Though standard methods for the heterotrophic cultivation of microalgae are known (see, for example, Miao and Wu, J. Biotechnology, 2004, 11:85-93 and Miao and Wu, Biosource Technology (2006) 97:841-846), the methods described herein introduce novel aspects to such methods, and it has been found that cultivating microalgal cultures under the heterotrophic growth conditions described herein provide favorable conditions for rapid propagation of high density microalgae cultures from which lipids, proteins, and algal biomass can be harvested, obtained, extracted, or otherwise isolated. Though the methods and systems described herein are generally described in the context of lipid or hydrocarbon-producing algae, the methods and systems are not so limited. As is detailed herein, a range of microalgae may be cultivated using the systems and methods described herein, and the culture conditions may be adjusted depending on the resources to be harvested. In particular, in certain embodiments, the culture conditions may be adjusted to emphasize production of biomass, proteins, or lipids. In certain embodiments, the culture conditions of the microalgae may be adjusted to increase production of select components or materials in the biomass. For example, conditions including, but not limited to, pH, temperature, nutrient composition, and/or nutrient concentrations may be modified to adjust or increase the production of select components or materials in the biomass.

Generally, in the methods described herein, an inoculum of microalgae may be introduced into a culture media contained within a fermentor. This introduction may be followed by a lag period (also referred to as a "lag phase") before the cells begin growth. Following the lag period, the growth rate may increase steadily and enter the log phase (also referred to as an "exponential phase"). The exponential phase, in turn, may be followed by a slowing of growth due to decreases in nutrients and/or increases in toxic substances. After such slowing, growth may stop, and the microalgae cells may enter a stationary phase or steady state, depending on the particular environment provided to the cells. Lipid production by the microalgae cells within culture may occur during the log phase or thereafter, including the stationary phase wherein nutrients may be supplied, or still available, to allow the continuation of lipid production in the absence of cell division.

The microalgae may be cultivated in quantities ranging from laboratory to commercial-scale volumes. Known fermentors, such as known steel fermentors, may be used to accommodate a wide range of culture volumes for heterotrophic cultivation of microalgae cultures according to the present description. A fermentor similar to those used in the production of beer and/or wine may be suitable, as are large, commercial-scale fermentors used in the production of ethanol. The fermentation may be carried out in large liquid volumes, such as in suspension cultures, and as described herein, the fermentation step may include starting with a small culture of cells which expand into a large biomass through a combination of cell growth and propagation.

A culture media suitable for heterotrophic growth of the microalgae may be included within the fermentor used in the methods described herein. Though the growth media may include solid and liquid components, the growth media may typically be an aqueous solution, suspension, dispersion, emulsion, or slurry that provides a favorable environment for the microalgae culture. Once the culture media contained within the fermentor is inoculated with a microalgae culture and growth of the microalgae begins, a fermentation broth is formed. The fermentation broth includes the growth media as well as non-living cellular material, waste products excreted by the microalgae, and lipids or other materials secreted by the microalgae. As used herein, the term "fermentation broth" does not include the fraction contained within the fermentor that is made up of whole, live cells of microalgae.

The inoculum of microalgae introduced into the fermentor may include a single species of microalgae or a combination of two or more species for co-cultivation. Again, various different species of microalgae may be suited for use in the methods described herein, and in particular embodiments, the microalgae cultivated may include one or more of the species of microalgae detailed herein. The inoculum of microalgae may be prepared or "primed" for heterotrophic propagation prior to inoculation into the fermentor. In some embodiments, the microalgae used to inoculate the fermentor may be produced by first cultivating the desired microalgae species under conditions for autotrophic propagation (such as in a photobioreactor). In certain such embodiments, standard conditions for autotrophic cultivation for the microalgae selected may be used. Where the inoculum of microalgae is produced by first cultivating the microalgae using autotrophic growth conditions, the autotrophic culture of microalgae may be propagated to provide a culture having from 1% to 4% algae solids content. In some embodiments, % algae solids content may be a measurement of biomass. Alternatively, the autotrophic culture may be propagated to provide a culture having an algae solids content of about 0.5 g/L to about 50 g/L. In particular embodiments, the culture may be propagated to provide a culture having an algae solids content selected from about 1 g/L to about 50 g/L, about 1 g/L to about 40 g/L, about 1 g/L to about 30 g/L, about 1 g/L to about 20 g/L, about 1 g/L to about 10 g/L, and about 1 g/L to about 6 g/L. In certain embodiments, algae solids content (g/L) may be a measurement of biomass. Once an autotrophic culture having the desired solids content is achieved, aliquots of the culture may be removed and concentrated (such as, for example, by centrifugation or filtration (e.g., by membrane filtration)). Where desired, the concentrated microalgae may be washed and reconcentrated. To form the inoculum to be introduced into the fermentor, autotrophically primed and concentrated microalgae may be resuspended in a selected medium to provide an inoculum of desired volume and cell density.

Once the fermentor is inoculated with the desired microalgae, cultivation or co-cultivation (where two or more species of microalgae are propagated) of the microalgae may proceed under controlled culture conditions. The culture conditions may be monitored and adjusted over time as the culture matures within the fermentor. As described herein, the temperature, pH, nutrient profile of the culture media, and oxygen flow into the microalgal culture may be controlled.

The culture media used in a dark phase fermentor may include appropriate nutrient sources for growth, propagation, and production of a targeted resource (e.g., algae biomass, protein, or lipid). In certain embodiments, the dark phase fermentor may include a non-transparent, or substantially non-transparent, enclosure (e.g., a tank or vessel). Appropriate nutrient sources for the culture media may include raw materials such as one or more of the following: a fixed carbon source, such as dextrose, glucose, fructose, sucrose, galactose, xylose, mannose, rhamnose, N-acetylglucosamine, glycerol, floridoside, glucuronic acid, corn starch, depolymerized cellulosic material, sugar cane, sugar beet, lactose, milk whey, or molasses; a fat source, such as fats or vegetable oils; a nitrogen source, such as protein, soybean meal, corn steep liquor, ammonia (pure or in salt form), nitrate or nitrate salt, molecular nitrogen, or a yeast extract; a phosphorus source, such as phosphate salts; and one or more coenzymes or coenzyme factors. Other carbon sources, in particular glucose sources, that may be utilized in the culture media include wheat, potato, rice, and sorghum.

In various embodiments, Fermaid® K (Scott Laboratories), a blended complex yeast nutrient, may be added or introduced to the culture media. Other blended complex yeast nutrients may also be utilized. In some embodiments, the blended complex yeast nutrient may comprise one or more of magnesium sulfate, calcium pantothenate, inactive yeast, thiamine, folic acid, niacin, and/or diammonium phosphate.

In certain embodiments, nutrient ferm (e.g., Nutrient Vit End™ (Scott Laboratories)), a specific inactivated yeast, may be added or introduced to the culture media. Other specific inactivated yeast(s) may also be utilized.

In some embodiments, ConcenTrace® Trace Mineral Drops (Trace Minerals Research), a trace mineral supplement, may be added or introduced to the culture media. Other trace mineral supplements may also be utilized. In various embodiments, the trace mineral supplement may comprise one or more of calcium (e.g., calcium carbonate), iron (e.g., iron glycinate), iodine, magnesium (e.g., magnesium oxide), chloride (e.g., potassium chloride), silicon, selenium, phosphorus, chromium, manganese, copper, molybdenum, zinc, vanadium, other ionic trace minerals, and/or other trace minerals. In various other embodiments, the trace mineral supplement may comprise one or more of aluminum, antimony, arsenic (e.g., inorganic arsenic), barium, beryllium, bismuth, boron, bromide, cadmium, calcium, carbonate, cerium, cesium, chloride, chromium, cobalt, copper, dysprosium, erbium, europium, fluoride, gadolinium, gallium, germanium, gold, hafnium, holmium, indium, iodine, iridium, iron, lanthanum, lead, lithium, lutetium, magnesium, manganese, mercury, molybdenum, neodymium, nickel, niobium, osmium, palladium, phosphorus, platinum, potassium, praseodymium, rhenium, rhodium, rubidium, ruthenium, samarium, scandium, selenium, silicon, silver, sodium, strontium, sulfate/sulfur, tantalum, tellurium, terbium, thallium, thorium, thulium, tin, titanium, tungsten, vanadium, ytterbium, yttrium, zinc, zirconium, and/or other naturally-occurring trace minerals (i.e., naturally-occurring trace minerals that may be found in seawater).

The one or more carbon source(s) may be supplied at a concentration of at least about 50 µM, at least about 100 µM, at least about 500 µM, at least about 5 mM, at least about 50 mM, and at least about 500 mM, of one or more exogenously provided fixed carbon source(s). Where used as the fixed carbon source, dextrose may be provided at a concentration selected from concentrations ranging from, for example, about 2.5 g/L to about 125 g/L. In particular embodiments utilizing dextrose as a fixed carbon source, the concentration of dextrose within the culture media may be selected from 2.5 g/L to 100 g/L, 5 g/L to 100 g/L, and 10 g/L to 100 g/L. In other such embodiments, the concentration of dextrose within the culture media may be selected from 2.5 g/L to 75 g/L, 5 g/L to 75 g/L, and 10 g/L to 75 g/L. In still further such embodiments, the concentration of dextrose within the culture media may be selected from 15 g/L to 65 g/L, 20 g/L to 55 g/L, and 25 g/L to 50 g/L. The amount of dextrose included in the culture media may be increased over time to ensure sufficient nutrients for desired growth or production characteristics. For example, upon inoculation of the fermentor with the microalgae to be cultivated, the culture media may include a concentration of dextrose ranging from, for example, 2.5 g/L to 10 g/L, with the concentration of dextrose being increased over the course of the cultivation process to a concentration ranging from, for example, 50 g/L to 100 g/L.

In some embodiments, a total amount or volume of the one or more carbon source(s) that may be used for, or during, a microalgae propagation may be determined. The total amount of the one or more carbon source(s) may be about 1000 g/10 L of fermentation broth. In some embodiments, the total amount of the one or more carbon source(s) may be from about 100 g/10 L to about 1000 g/10 L of fermentation broth, from about 250 g/10 L to about 1000 g/10 L of fermentation broth, from about 500 g/10 L to about 1000 g/10 L of fermentation broth, from about 750 g/10 L to about 1000 g/10 L of fermentation broth, and from about 900 g/10 L to about 1000 g/10 L of fermentation broth.

In various embodiments, the total amount of the one or more carbon source(s), as described, may not be introduced to the culture media in a single addition or at a single time point. For example, the total amount of the one or more carbon source(s) may be divided into more than one aliquot. Each aliquot of the one or more carbon source(s) may then be introduced to the culture media and/or fermentation broth at various time points over the course of the microalgae propagation. For example, a first aliquot of the one or more carbon source(s) may be introduced to the inoculated culture media at time point zero, a second aliquot of the one or more carbon source(s) may be introduced to the inoculated culture media at about two hours after time point zero, a third aliquot of the one or more carbon source(s) may be introduced to the inoculated culture media at about four hours after time point zero, etc. Stated another way, an aliquot of the one or more carbon source(s) may be introduced to the inoculated culture media about every 30 minutes over the course of the propagation, about every hour over the course of the propagation, about every two hours over the course of the propagation, about every three hours over the course of the propagation, and so on. In certain embodiments, aliquots of the one or more carbon source(s) may be added at variable time points over the course of the propagation. For example, the time span between introductions of each aliquot of the one or more carbon source(s) may vary over the course of the propagation.

In certain embodiments, glycerol (also referred to herein as "glycerin") may be included as a fixed carbon source. It may be included alone or in combination with one or more other fixed carbon sources. Where it is included in the culture media, it may be included in the culture media in an amount ranging from about 0.05% to about 15% (v/v). In particular embodiments, the amount of glycerin included in the culture media may be selected from about 1% to about 10% (v/v). In even further embodiments, glycerin may be included in the culture media in an amount selected from about 1%, 2%, 3%, 4%, 5%, 6%, 7%, 8%, 9%, or 10% (v/v).

The temperature of the culture within the fermentor may be monitored and maintained within a desired range. Generally, the temperature may be maintained, for example, between about 15° C. and about 40° C. In specific embodiments, the temperature may be maintained within a range selected from between about 15° C. and about 35° C., between about 15° C. and about 30° C., between about 15° C. and about 25° C., between about 25° C. and about 35° C., between about 30° C. and about 35° C., and between about 30° C. and about 32° C.

The pH of the microalgal culture within the fermentor may also be controlled and maintained between about a pH of 4.0 and about a pH of 9.5. In specific embodiments, the pH may be maintained at a pH range selected from one of about a pH of 4.5 to about a pH of 7.5, about a pH of 5.0 to about a pH of 7.0, about a pH of 5.5 to about a pH of 6.5, about a pH of 6.0 to about a pH of 9.5, and about a pH of 7.0 to about a pH of 9.5. The pH of the microalgae culture may be maintained through use of an aqueous buffer system. Any buffer system compatible with the growth of microalgae may be used, and in specific embodiments, aqueous ammonia ($NH_4OH$) and phosphoric acid ($H_3PO_4$) may be included in the culture media to buffer the culture to a desired pH. Where used as a buffer system, ammonia may also serve as a source of nitrogen and phosphoric acid may also serve as a source of phosphorous. For example, ammonia may be included in the culture media in sufficient amounts to provide between about 1.0 g and about 10 g $N_2$ per each 100 g of algae biomass. Additionally, phosphoric acid may be included in the culture media in sufficient amounts to provide between about 1.0 g and about 5 g $P_2O_5$ per each 100 g of algae biomass. In specific embodiments, the culture media may be maintained to include sufficient ammonia to provide a concentration of $N_2$ within the fermentation broth of between about 2 g and about 7 g $N_2$ per 100 g of algae biomass and sufficient phosphoric acid to provide a concentration of $P_2O_5$ within the fermentation broth of between about 1.0 g and about 3 g $P_2O_5$ per 100 g of algae biomass over the course of the cultivation process.

The amount of oxygen within the fermented culture may also be controlled throughout the fermentation process. Specifically, it has been found that delivering oxygen ($O_2$) into the microalgae culture as it grows and propagates within the fermentor may lead to increased lipid production. In some embodiments, the oxygen may be a concentrated oxygen gas. For example the oxygen gas may be between about 75% and about 100% oxygen, between about 80% and about 100% oxygen, between about 90% and about 100% oxygen, between about 90% and about 98% oxygen, about 95% oxygen, and about 98% oxygen. In certain embodiments, the oxygen may be delivered from an oxygen generator or from an oxygen canister. In methods according to the present description, oxygen may be delivered into the culture at a rate of between about 0.1 L/minute to about 2.5 L/minute for each 10 L total volume of fermentation broth. In specific embodiments, oxygen may be fed into the culture at a rate selected from between about 0.25 L/minute and about 4.5 L/minute, between about 0.25 L/minute and about 2.0 L/minute, between about 0.25 L/minute and about 1.5 L/minute, and between about 0.35 L/minute and about 1.5 L/minute, each per 10 L total volume of fermentation broth. The delivery of oxygen into the culture may be accomplished by any desirable means. For example, a gas line may be provided into the fermentor that introduces oxygen into the culture such that it bubbles up and or diffuses through the fermentation broth. Moreover, the oxygen may be delivered to the culture continuously, or it may be delivered for one or more selected time periods at different points during the propagation or maintenance of the microalgae culture within the fermentor.

The microalgae culture may be cultivated within the fermentor for a minimum residence time, and high concentrations of microalgae within the fermentation broth may be quickly achieved (e.g., in less than 48 hours) using the conditions described herein. In specific embodiments, the microalgae culture may be maintained within the fermentor for a period of time selected from at least 24 hours, at least 36 hours, at least 48 hours, and at least 60 hours. In certain such embodiments, the microalgae culture may be maintained within the fermentor for a period of time selected from at least 20 hours, at least 30 hours, at least 40 hours, at least 50 hours, and at least 60 hours. Such minimum residence times, in combination with the cultivation conditions detailed herein may result in high concentrations of microalgae cells. For example, in certain embodiments, the methods described herein may result in microalgae cultures exhibiting a concentration of microalgae ranging from 70-100 g/L algae, 75-95 g/L algae, and 80-90 g/L algae within 48 hours.

Other components or materials may be introduced into the culture media used in the fermentor to preserve and or achieve desired growth, propagation, and/or lipid production from the microalgae. In one example, it has been found that introducing brewers hops into the culture media may work to protect the culture against growth of or infection by undesirable microorganisms, such as yeast or bacteria, which may reduce or inhibit growth, health, and propagation of microalgae. Where brewers hops are introduced into the culture media, approximately 5 grams to 500 grams of hops may be used per liter of microalgae culture (5-500 g/L). In specific embodiments, about 1, 2, 3, 4, 5, 6, 7, 8, 9, 10, 15, 20, 25, 50, 75, 100, 125, 150, 175, 200, 225, 250, 275, 300, 325, 350, 375, 400, 425, 450, 475, and 500 grams of hops may be used per liter of microalgae culture.

In particular embodiments, the culture media and conditions within the fermentor may be tailored to produce microalgae cultures that favor production of, for example, algae biomass, protein, or lipid. Where a microalgae culture providing both high density algae biomass and high levels of lipid production may be desired, in certain embodiments, the pH of the culture media may be maintained at between about 5.4 and 7.0, the temperature may be maintained at between about 18° C. and 27° C., and oxygen may be delivered to the culture at a rate of about 1.5 L/min per 10 L of fermentation broth.

Where a microalgae culture providing both high density algae biomass and high levels of protein production may be desired, in certain embodiments, the pH of the culture media may be maintained at between about 6.8 and 9.2, the temperature may be maintained at between about 21° C. and 33° C., and oxygen may be delivered to the culture at a rate of about 0.35 L/min per 10 L of fermentation broth. Where a microalgae culture providing increased algae biomass may be desired, in certain embodiments, the pH of the culture media may be maintained at between about 5.5 and 6.2, the temperature may be maintained at between about 21° C. and 28° C., and oxygen may be delivered to the culture at a rate of about 1.0 L/min per 10 L of fermentation broth. In each such embodiment, the cultivation conditions may not only provide favorable production of the targeted product (i.e., lipid, protein, or biomass), but they may also result in microalgae cultures exhibiting a concentration of microalgae selected from a range of about 70-100 g/L algae, about 75-95 g/L algae, and about 80-90 g/L algae within 48 hours.

Where the process conditions may be selected to favor lipid production, such conditions may drive lipid production as a first order function of the microalgae. Three different markers of lipid productivity (dry cell weight per liter, grams per liter of extracellular lipid, and percentage of dry cell weight as lipid) may be considered and monitored as part of the methods described herein. Methods according to the present description may provide desirable improvements in the grams per liter of extracellular lipid and the percentage of dry cell weight as lipid within cultures of microalgae. In particular embodiments, the methods described herein may result in cultures of microalgae wherein the microalgae include at least 25% lipid as a percentage of dry cell weight. For example, the methods described herein may result in cultures of microalgae wherein the microalgae include a percentage of lipid by dry cell weight selected from at least 25%, at least 30%, at least 35%, at least 40%, at least 45%, at least 50%, at least 55%, at least 60%, at least 65%, at least 70%, at least 75%, and at least 80%. Moreover, in some embodiments, methods according to the present disclosure may result in a fermentation broth that may include at least 10% (v/v) lipid. For example, the methods described herein may result in microalgae cultures that secrete high levels of lipid resulting in a fermentation broth that includes an amount of lipid selected from at least 10% (v/v), at least 15% (v/v), at least 20% (v/v), and at least 25% (v/v). In even further embodiments, the methods described herein may result in cultures of microalgae wherein the microalgae produce both high levels of intracellular lipid (i.e., high levels of lipid contained within the microalgae by dry cell weight) and high levels of extracellular lipid contained within the fermentation broth.

In some embodiments, an increase in microalgae biomass may correlate with an increase in microalgae lipid production. For example, as the biomass of a microalgae culture increases the amount of lipid produced by the microalgae in the microalgae culture may also increase. In certain embodiments, the biomass of the microalgae culture may increase at about the same rate as the increase in the rate of lipid production by the microalgae. In certain other embodiments, the biomass of the microalgae culture may increase at a greater rate than the rate of lipid production by the microalgae. In yet certain other embodiments, the biomass of the microalgae culture may increase at a lower rate than the rate of lipid production by the microalgae.

FIGS. 1-6 are micrographs depicting samples of *Chlorella vulgaris*, wherein the *Chlorella vulgaris* samples were cultivated in 30 L of fermentation broth under heterotrophic growth conditions and with the introduction of oxygen. The contents of the fermentation broth were as described in Example 1 below. FIG. 1 is a micrograph depicting a sample of microalgae prior to, or at the onset of, being cultivated under heterotrophic growth conditions and with the introduction of oxygen according to an embodiment of the present disclosure. The micrograph was acquired at 0900 hours on day 1 at a magnification of 400×. As depicted in FIG. 1, algae cells are visible comprising levels of lipid that may be comparable to the levels of lipid produced by microalgae cells cultivated under autotrophic growth conditions. Further, the surrounding fermentation broth appears to be substantially clear and substantially free of lipid.

Figure 2:
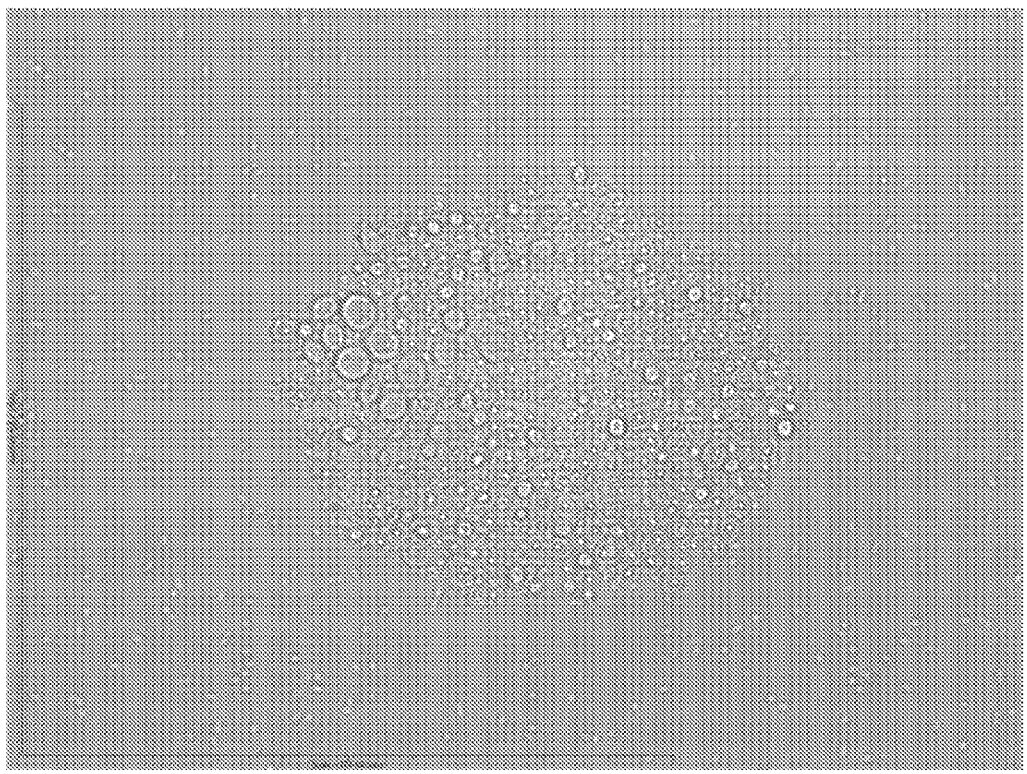
FIG. 2 is a micrograph depicting a sample of microalgae cultivated under heterotrophic growth conditions and with the introduction of oxygen according to an embodiment of the present disclosure. The micrograph was acquired at 2000 hours on day 1 at a magnification of 1000×.

FIG. 2 is a micrograph depicting a sample of microalgae cultivated under heterotrophic growth conditions and with the introduction of oxygen according to an embodiment of the present disclosure. The micrograph was acquired at 2000 hours on day 1 at a magnification of 1000×. FIG. 2 depicts a cluster of algae cells, wherein the individual cells may be larger, on average, than the individual cells of FIG. 1. It may also be seen in FIG. 2 that at least some of the microalgae cells may be abnormal in size (i.e., larger than normal). Further, lipids are visible in FIG. 2 as the substantially clear dots disposed around the microalgae cells.

Figure 3:
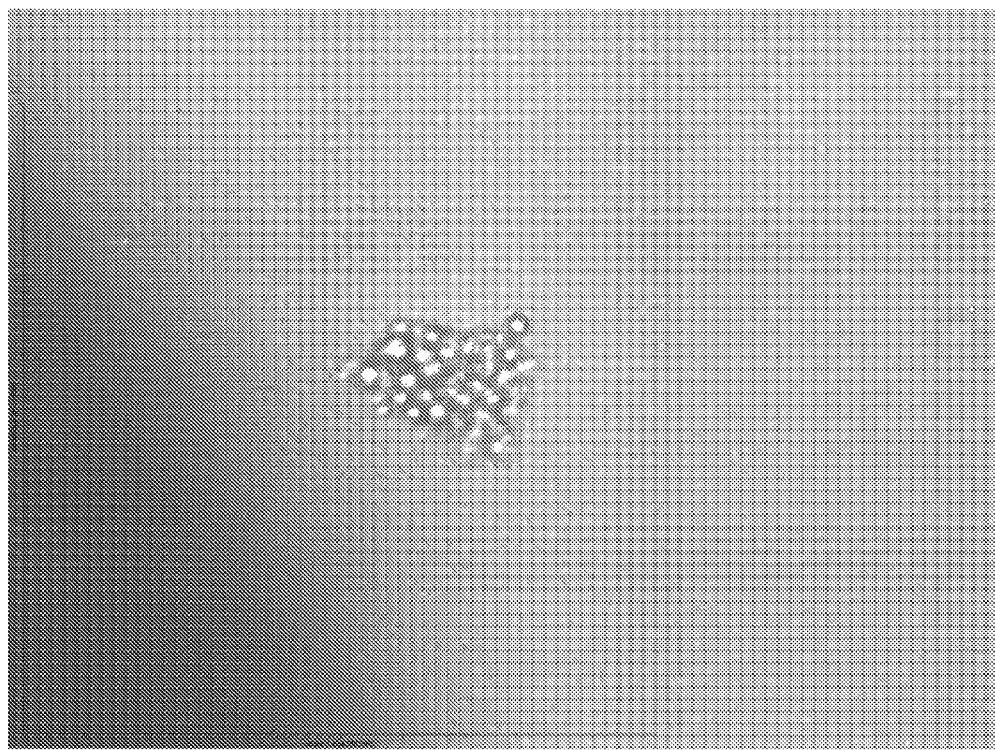
FIG. 3 is a micrograph depicting a sample of microalgae cultivated under heterotrophic growth conditions and with the introduction of oxygen according to an embodiment of the present disclosure. The micrograph was acquired at 0800 hours on day 2 at a magnification of 1000×.

FIG. 3 is a micrograph depicting a sample of microalgae cultivated under heterotrophic growth conditions and with the introduction of oxygen according to an embodiment of the present disclosure. The micrograph was acquired at 0800 hours on day 2 at a magnification of 1000×. FIG. 3 depicts an increase in the number of lipids disposed around the clusters of microalgae cells in relation to the microalgae cells of FIGS. 1 and 2. Also visible are new microalgae cells, which may be small but fatty.

Figure 4:
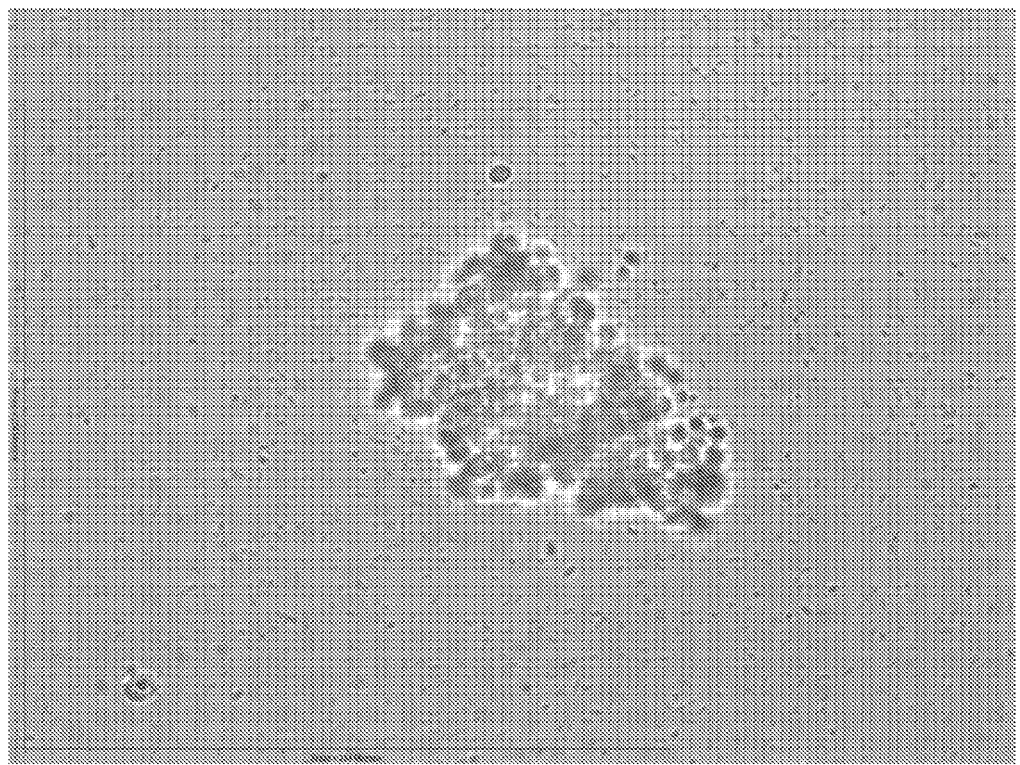
FIG. 4 is a micrograph depicting a sample of microalgae cultivated under heterotrophic growth conditions and with the introduction of oxygen according to an embodiment of the present disclosure. The micrograph was acquired at 1000 hours on day 2 at a magnification of 1000×.

FIG. 4 is a micrograph depicting a sample of microalgae cultivated under heterotrophic growth conditions and with the introduction of oxygen according to an embodiment of the present disclosure. The micrograph was acquired at 1000 hours on day 2 at a magnification of 1000×. FIG. 4 shows that the extracellular space has been substantially filled with lipids. Additionally, the cells may be larger than microalgae cells cultivated under autotrophic growth conditions and the cells may also comprise a substantial amount of lipid, wherein at least some of the cells may be predominantly composed of lipid.

Figure 5:
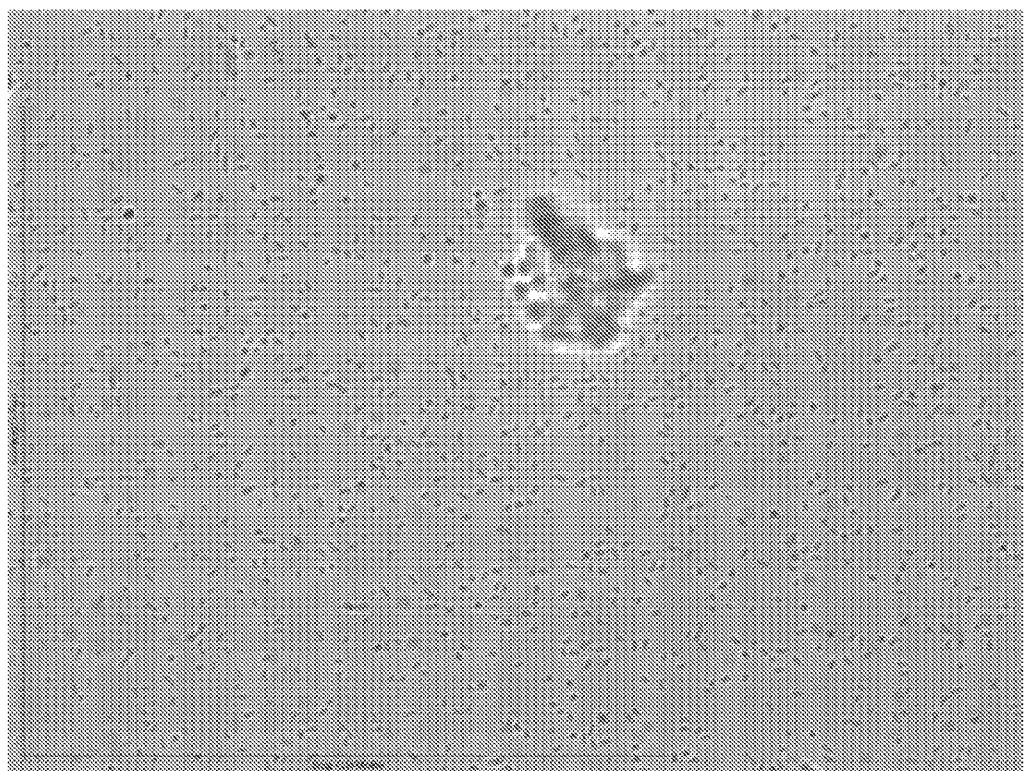
FIG. 5 is a micrograph depicting a sample of microalgae cultivated under heterotrophic growth conditions and with the introduction of oxygen according to an embodiment of the present disclosure. The micrograph was acquired at 1200 hours on day 2 at a magnification of 1000×.

FIG. 5 is a micrograph depicting a sample of microalgae cultivated under heterotrophic growth conditions and with the introduction of oxygen according to an embodiment of the present disclosure. The micrograph was acquired at 1200 hours on day 2 at a magnification of 1000×. The microalgae cells in FIG. 5 may also be larger than cells cultivated under autotrophic growth conditions and may also comprise a substantial amount of lipid. Again, at least some cells may be predominantly composed of lipid. Microalgae cell clumping or clustering, due at least in part to the presence of lipid, is also visible.

Figure 6:
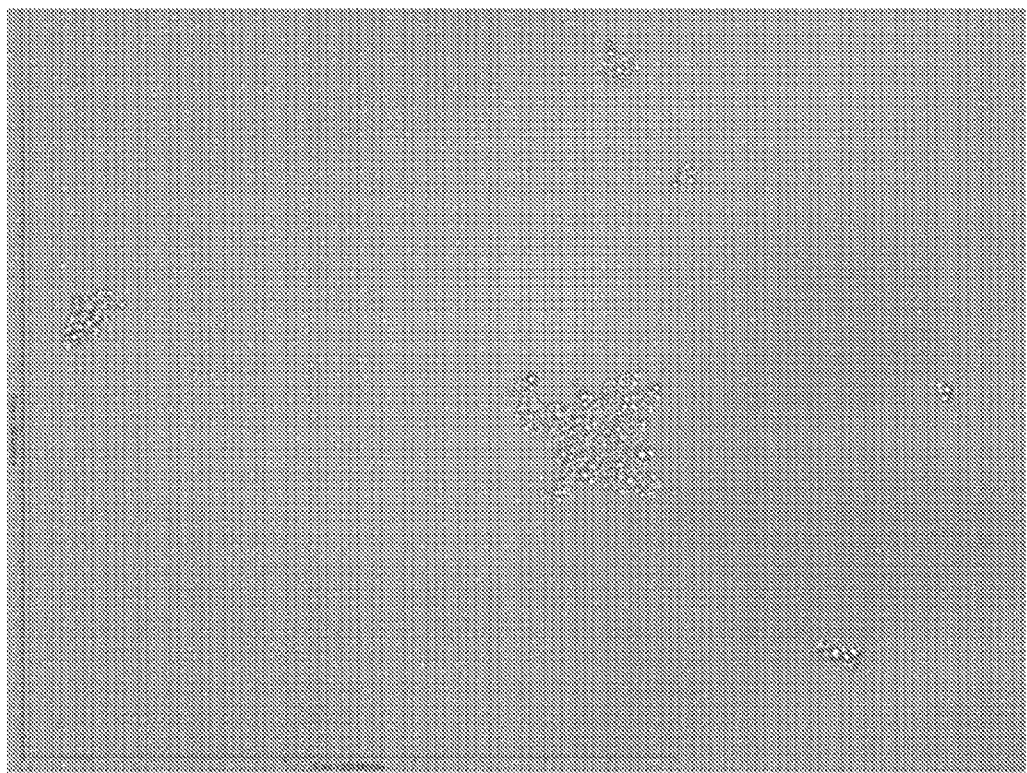
FIG. 6 is a micrograph depicting a sample of microalgae cultivated under heterotrophic growth conditions and with the introduction of oxygen according to an embodiment of the present disclosure. The micrograph was acquired at 0800 hours on day 3 at a magnification of 400×.

FIG. 6 is a micrograph depicting a sample of microalgae cultivated under heterotrophic growth conditions and with the introduction of oxygen according to an embodiment of the present disclosure. The micrograph was acquired at 0800 hours on day 3 at a magnification of 400×. At this time point it may be determined that at least some of the microalgae cells have ceased growing. At about this time point the growth of the microalgae calls may also have plateaued.

With reference to FIGS. 1-6, as one focuses through the layers of microalgae cells, substantially "shiny" centers that may comprise lipids may be visible. As one shifts the focus, the same cells may appear darker as the focus may now be directed to the cell walls. Throughout the time course, as depicted in FIGS. 1-6, the "shiny" centers may generally increase in size as the microalgae cultivation progresses.

In some embodiments, methods of inducing lipid production in microalgae may comprise inoculating a culture media with microalgae and propagating the microalgae under heterotrophic growth conditions. The heterotrophic growth conditions may comprise inhibiting, limiting, or reducing exposure of the inoculated culture media to light. In some embodiments, the inoculated culture media may be subjected to a substantially dark environment. For example, the inoculated culture media may be contained in a non-transparent, or substantially non-transparent, enclosure. In various embodiments, methods of inducing lipid production in microalgae may further comprise delivering or introducing oxygen into the inoculated culture media, such that the microalgae produce lipids at a greater rate than may be produced by the microalgae under standard growth conditions or autotrophic growth conditions. In certain embodiments, methods of inducing lipid production in microalgae may further comprise cultivating the microalgae under autotrophic growth conditions prior to propagating the microalgae under heterotrophic growth conditions.

In various embodiments, oxygen may be delivered or introduced into the inoculated culture media at a rate of between about 0.1 L/minute to about 2.5 L/minute for each 10 L volume of inoculated culture media. Other suitable rates of such oxygen delivery are discussed above. Additionally, oxygen may be delivered into the inoculated culture media via a gas line such that the oxygen diffuses through the inoculated culture media. In some embodiments, the oxygen may be delivered substantially continuously into the inoculated culture media, while, in some other embodiments, the oxygen may be delivered into the inoculated culture media for one or more time periods during the propagation of the microalgae.

In certain embodiments, the methods disclosed herein may further comprise monitoring a temperature of the inoculated culture media, and maintaining the temperature of the inoculated culture media within a suitable range of temperatures (La, from about 15° C. to about 40° C.). In various embodiments, the methods may further comprise monitoring a pH of the inoculated culture media, and maintaining the pH of the inoculated culture media within a suitable pH range (i.e., from about a pH of 4.0 to about a pH of 9.5). The pH may be maintained by an aqueous buffer system or another suitable mechanism or system, as described above. Also, as discussed above, other suitable ranges of temperature and/or pH are also within the scope of this disclosure. Upon introduction of the microalgae inoculation (i.e., at time zero), a sample of the culture may be collected and processed to establish starting data points for various conditions (i.e., pH, temperature, etc.). In certain embodiments, the inoculated culture media may be contained in a dark phase fermentor, which may be disposed in a dark, or substantially dark, room. In certain embodiments, the dark phase fermentor may be configured such that a culture media disposed in the fermentor is not exposed to light. In various embodiments, the dark phase fermentor may be configured such that a culture media disposed in the fermentor is exposed to limited or reduced levels of light. The temperature of the room wherein the dark phase fermentor is placed may be adjusted to assist the dark phase fermentor to maintain a desired temperature. Other mechanisms, as discussed above, may also be used to adjust or maintain the culture at a desired temperature.

In various embodiments, the microalgae may be selected from at least one of *Ankistrodesmus* species, *Botryococcus* species, *Chlorella* species, *Crypthecodinium* species, *Cyclotella* species, *Dunaliella* species, *Hantzschia* species, *Nannochloris* species, *Nannochloropsis* species, *Neochloris* species, *Nitzschia* species, *Phaeodactylum* species, *Scenedesmus* species, *Stichococcus* species, *Tetraselmis* species, *Thalassiosira* species, and/or *Schizochytrium* species. In certain embodiments, the microalgae may be selected from at least one of *Chlorella fusca*, *Chlorella protothecoides*, *Chlorella pyrenoidosa*, *Chlorella kessleri*, *Chlorella vulgaris*, *Chlorella saccharophila*, *Chlorella sorokiniana*, and/or *Chlorella effipsoidea*.

In some embodiments, the culture media may be disposed within a fermentor. As discussed above, the culture media may comprise one or more of a carbon source, a fat source, a nitrogen source, a phosphorus source, and/or one or more coenzymes or coenzyme factors. The carbon source may be selected from at least one of dextrose, glucose, fructose, sucrose, galactose, xylose, mannose, rhamnose, N-acetylglucosamine, glycerol, floridoside, glucuronic acid, corn starch, depolymerized cellulosic material, sugar cane, sugar beet, lactose, milk whey, and/or molasses.

In some embodiments, the fat source may be selected from at least one of fats and/or vegetable oils. Likewise, the nitrogen source may be selected from at least one of protein, soybean meal, corn steep liquor, ammonia, nitrate, nitrate salt, molecular nitrogen, and/or yeast extract. Other suitable fat sources and nitrogen sources, as discussed above, are also within the scope of this disclosure.

In various embodiments, methods of inducing protein production in microalgae may also comprise inoculating a culture media with microalgae and propagating the microalgae under heterotrophic growth conditions. As discussed above, the heterotrophic growth conditions may comprise inhibiting, limiting, or reducing exposure of the inoculated culture media to light. In various embodiments, methods of inducing protein production in microalgae may further comprise delivering oxygen into the inoculated culture media, such that the microalgae produces protein at a greater rate than is produced by the microalgae under standard growth conditions or autotrophic growth conditions.

In certain embodiments, methods of inducing protein production in microalgae may further comprise maintaining a pH of the inoculated culture media between about a pH of 6.8 and about a pH of 9.2. The method may also comprise maintaining a temperature of the inoculated culture media between about 21° C. and about 33° C. In certain embodiments, the method may further comprise delivering oxygen into the inoculated culture media at a rate of between about 0.5 L/minute to about 4.0 L/minute per 10 L of inoculated culture media.

In some embodiments, methods of inducing production of increased microalgae biomass may comprise inoculating a culture media with microalgae and propagating the microalgae under heterotrophic growth conditions. Again, as discussed above, the heterotrophic growth conditions may comprise inhibiting, limiting, or reducing exposure of the inoculated culture media to light. In certain embodiments, methods of inducing production of increased microalgae biomass may further comprise delivering oxygen into the inoculated culture media, such that the microalgae biomass increases at a greater rate than by the microalgae under standard growth conditions or autotrophic growth conditions.

In certain embodiments, methods of inducing production of increased microalgae biomass may further comprise maintaining a pH of the inoculated culture media between about a pH of 5.5 and about a pH of 6.2. The method may also comprise maintaining a temperature of the inoculated culture media between about 21° C. and about 28° C. In various embodiments, the method may further comprise delivering oxygen into the inoculated culture media at a rate of between about 0.5 L/minute to about 4.0 L/minute per 10 L of inoculated culture media.

In certain embodiments, one or more lipids and/or proteins may be obtained, extracted, isolated and/or purified from microalgae cultivated under one or more of the methods disclosed herein.

In various embodiments, the inoculum of microalgae introduced to the dark phase fermentor may be green algae (e.g., the microalgae may have a green, or substantially green color). In some embodiments, green algae are in a state wherein the green algae perform photosynthesis. Upon cultivation under the above-described conditions or methods, the green algae may be converted to blonde algae. For example, the blonde algae may have a substantially white color.

In certain embodiments, blonde algae may be converted or reverted to green algae. Blonde algae may not survive beyond about 56 hours and may be converted or reverted to green algae within about 56 hours. After about 56 hours, blonde algae may die if it is not returned to propagation under autotrophic growth conditions. In some embodiments, the conversion or reversion of blonde algae to green algae may comprise collecting a sample of blonde algae and introducing or returning the sample of blonde algae to a photobioreactor. For example, the sample of blonde algae may be exposed to or fed nutrients including, but not limited to, carbon dioxide, diammonium phosphate, and/or sunlight (or another suitable light source). Conversion or reversion of blonde algae to green algae may occur within about two weeks. In some embodiments, the conversion of blonde algae to green algae may occur within about one week to about four weeks, within about 1.5 weeks to about 3.5 weeks, within about 1.5 weeks to about 3 weeks, or within about 2 weeks to about 2.5 weeks. In various embodiments, introduction of carbon dioxide and/or aeration may initiate or restart photosynthetic processes in a blonde algae sample or culture. In certain embodiments, green algae may be converted to blonde algae within about two hours of the introduction of oxygen into the culture media, as described above. In certain other embodiments, green algae may be converted to blonde algae within about two hours to about 4 hours of the introduction of oxygen into the culture media or within about two hours to about 6 hours of the introduction of oxygen into the culture media.

In some embodiments, the process of converting green algae to blonde algae may stress the algae. The process of converting green algae to blonde algae may induce the algae to suppress, abandon, or reduce photosynthetic mechanisms or processes. In certain embodiments, instead of creating or generating sugars and/or oxygen, the algae cells may be exposed or overexposed to their natural byproducts and some algae cells may die and some algae cells may survive. In some embodiments, at least a portion of the algae cells that survive may abandon natural processes (i.e., photosynthesis) and use carbon and/or oxygen to create or generate lipids. This process may be referred to as "hyperproduction." For example, blonde algae may enter a condition or state of hyperproduction. In some embodiments, when blonde algae commence or enter hyperproduction, the blonde algae may produce one or more types of lipid at a high rate (i.e., at a rate that is higher than a wild type rate). During fermentation, blonde algae may experience stress such that the blonde algae produce increased levels of lipids in comparison to non-stressed algae. In certain embodiments, hyperproduction of lipids may eventually plateau or substantially stop. For example, the blonde algae may be over-stressed or a substantially portion of the blonde algae cells may become stressed and blonde algae cells may be unable to continue to survive.

In some embodiments, the growth rate of blonde algae, or microalgae cultivated under heterotrophic growth conditions with the introduction of oxygen, may rapidly accelerate (i.e., the number of algae cells in the solution may multiply). At about the same time, or substantially the same time, blonde algae cells, or microalgae cells cultivated under heterotrophic growth conditions with the introduction of oxygen, may produce lipids at an increased rate. For example, the rate of lipid production in blonde algae, or microalgae cultivated under heterotrophic growth conditions with the introduction of oxygen, may be greater than the rate of lipid production in green algae, or microalgae, cultivated under autotrophic growth conditions. As blonde algae produce lipids, the lipids may be released or expelled from blonde algae cells and into the surrounding solution. Likewise, as microalgae cultivated under heterotrophic growth conditions with the introduction of oxygen produce lipids, the lipids may be released or expelled from the microalgae cells and into the surrounding solution. The increased production of lipids may continue until a blonde algae conversion process is stopped or the cultivation of the microalgae under heterotrophic growth conditions with the introduction of oxygen is stopped. In certain embodiments, the total volume of culture media may be from about 10% to about 20% lipid and the blonde algae cells disposed in the culture media, or the microalgae cells cultivated under heterotrophic growth conditions with the introduction of oxygen, may comprise from about 60% to about 80% lipid content. In contrast, *Chlorella* species propagated under autotrophic growth conditions generally comprise from about 5% to about 14% lipid content and do not generally expel a significant amount of lipid. Such increased production of lipid in blonde algae, or microalgae cultivated under heterotrophic growth conditions with the introduction of oxygen, may occur within about 48 hours.

Recovering Lipids Produced by Microalgae

After the cultivation process is complete, the microalgae may be separated from the fermentation broth and biomass and/or the proteins or lipids produced by the microalgae may be harvested. Lipids (e.g., hydrocarbons, fatty acids, aldehydes, alcohols, and alkanes) produced by microalgae processed according to the methods described herein may be harvested, or otherwise collected, by any suitable means. Once collected, the lipids and/or hydrocarbons may be further refined to produce, for example, oils, fuels, or oleochemicals.

Where the extracellular lipids present in the fermentation broth are to be collected, the fermentation broth may be separated from the microalgae and other organic material by filtration and the filtered fermentation broth containing the lipids may then be centrifuged. Centrifugation separates the lipids in a hydrophobic layer distinct from an aqueous layer within which hydrophilic contaminants tend to partition, and if solid particulates remain within the fermentation broth after filtration, centrifugation may also separate such materials as a precipitate distinct from the lipid material. Additionally, material containing cell or cell fractions may be treated with proteases to degrade contaminating proteins before or after centrifugation. In some instances the contaminating proteins may be associated, possibly covalently, to hydrocarbons or hydrocarbon precursors, which may form hydrocarbons upon removal of the protein. In other instances the hydrocarbon molecules may be in a preparation that also contains proteins. Proteases may be added to hydrocarbon preparations to degrade proteins (for example, the protease from *Streptomyces griseus* can be used (Sigma-Aldrich catalog number P5147)). After digestion, the hydrocarbons may be purified from residual proteins, peptide fragments, and amino acids. This purification can be accomplished, for example, by methods such as centrifugation and filtration.

Because the methods described herein may result in high concentrations of extracellular lipids, in some embodiments, recovery of the lipids may be carried out in such a way that the extracellular lipids may be isolated in vivo from living microalgae cells, which may then be returned to a bioreactor for continued use according to the methods described herein (e.g., for use as a starting point for preparing an inoculum of microalgae to be introduced into a fermentor). In particular embodiments, separation of the microalgae from extracellular lipid present in the growth medium may be carried out by exposure of the cells, in an otherwise sterile environment, to a non-toxic extraction solvent, followed by separation of the living cells and the hydrophobic fraction of extraction solvent and lipids, wherein the separated living cells may then be returned to a culture container such as a fermentor or photobioreactor (see Biotechnol Bioeng. 2004 Dec. 5; 88(5):593-600 and Biotechnol Bioeng. 2004 Mar. 5; 85(5): 475-81).

Lipids produced according to the methods described herein may also be isolated by whole cell extraction. The cells may first be disrupted, and intracellular and cell membrane/cell wall-associated hydrocarbons as well as extracellular hydrocarbons may be collected from the whole cell mass, such as by use of centrifugation as described above. The step of lysing a microorganism may be achieved by any convenient means, including heat-induced lysis, adding a base, adding an acid, using enzymes such as proteases and polysaccharide degradation enzymes such as amylases, using ultrasound, mechanical lysis, using osmotic shock, infection with a lytic virus, and/or expression of one or more lytic genes. Lysis may be performed to release intracellular molecules which have been produced by the microorganism. Each of these methods for lysing a microorganism may be used as a single method or in combination simultaneously or sequentially. In some embodiments, after completion of cultivation, the microalgae may be separated from the fermentation broth by centrifugation to generate a concentrated paste. Centrifugation may not remove significant amounts of intracellular water from the microorganisms and may not be a drying step. The biomass may then be washed with a washing solution (e.g., DI water) to rid the biomass of fermentation broth and debris. Optionally, the washed microalgal biomass may also be dried (oven dried, lyophilized, etc.) prior to cell disruption. Alternatively, cells may be lysed without separation from some or all of the fermentation broth when the fermentation is complete. For example, the cells can be at a ratio of less than 1:1 (v:v) cells to extracellular liquid when the cells are lysed.

Various methods are available for separating hydrocarbons and lipids from cellular lysates. For example, lipids may be extracted with a hydrophobic solvent such as hexane (see Frenzetal. 1989, Enzyme Microb. Technol., 11:717). Typically, the organic solvent may be added directly to the lysate without prior separation of the lysate components. In one embodiment, the lysate generated by one or more of the methods described above may be contacted with an organic solvent for a period of time sufficient to allow the lipid and/or hydrocarbon components to form a solution with the organic solvent. In some cases, the solution may then be further refined to recover specific desired lipid or hydrocarbon components. Solvent extraction methods, such as those using hexane as the solvent, are well known in the art. Lipids may also be extracted using liquefaction (see, for example, Sawayama, et al. 1999, Biomass and Bioenergy 17:33-39 and Inoue, et al. 1993, Biomass Bioenergy 6(4):269-274); oil liquefaction (see, for example, Minowa, et al. 1995, Fuel 74(12):1735-1738); and supercritical $CO_2$ extraction (see, for example, Mendes, et al. 2003, Inorganica Chimica Acta 356:328-334).

EXAMPLES

The following examples are illustrative of disclosed methods and compositions. In light of this disclosure, those of skill in the art will recognize that variations of these examples and other examples of the disclosed methods and compositions would be possible without undue experimentation.

Example 1

Various cultures of microalgae were prepared according to the methods described herein. In each culture, 5-50 ml of a microalgae inoculum was suspended in a fermentor in volumes of culture media varying from 10 L to 30 L. The microalgae inoculum were prepared using concentrated slurries of autotrophically cultured *Nannochloropsis* together with *Chlorella plethocoides* and exhibited a microalgae solids content ranging from 2 g/L to 4 g/L. For a volume of 30 L, the culture media comprised:

| | |
|---|---|
| Water | to 30 L volume |
| Sterile dextrose | 1 kg |
| Autolysed yeast extract | 15 g |
| Diammonium phosphate | 10 g |
| $H_3PO_4$ (25% sol) | to adjust pH 5-6 at start |
| $NH_4OH$ sol | to adjust pH |
| Coenzyme solution | 20 g |
| Glycol solution | 50 g |
| Hops (optional) | 222 g (about 7-8 g/L hops) |

In each instance, the culture media and microalgae culture were mixed in the fermentor and maintained for the initial 24 hours at a temperature ranging from approximately 18-35° C., and pH of between 3.5 and 9.5. $O_2$ was bubbled through the microalgae culture during the propagation time (20 hours to 30 hours) at a flow rate of approximately 0.1-1.0 L/min per each 10 L of cultured microalgae. The resulting microalgae biomass ranged from approximately 45 g/L to approximately 85 g/L, with lipid accounting for as much as 40% to 70% of the microalgae dry cell weight and at least 13% to 21% (v/v) of the fermentation broth.

Example 2

Ten (10) propagations of *Chlorella* were prepared to optimize the production of microalgae biomass. Table 1 depicts the average volume (in liters) of the inoculated culture media at various time points (e.g., 0 hours, 4 hours, 6 hours, etc.) of the 10 propagations. The average amount of sugar (in grams) introduced into the inoculated culture media at various time points is also shown. The sugar was introduced as a nutrient source for the microalgae. The amount of ammonia (in ml, diluted in solution to give 100 g/L) introduced into the inoculated culture media at various time points is also shown. The ammonia was introduced to adjust the pH of the inoculated culture media.

With continued reference to Table 1, a starting pH at various time points is depicted followed by an ending pH (i.e., after ammonia was used to adjust the pH). The "CT mm" column indicates the height of the microalgae mass, or biomass, inside a 15 ml centrifuge tube after centrifugation of the sample. Each sample had a volume of about 15 ml, and was centrifuged, or spun, for about 10 minutes at about 5000 rpm. The temperature in Fahrenheit (° F.) at specified time points is also indicated. The final column (CT ml A75) represents a conversion from height to volume of the microalgae mass collected in the bottom of the centrifuge tubes. A75 refers to the microalgae mass, as a collection of algae in the bottom of a centrifuge tube, upon centrifugation, is about 75% algae (i.e., A75) and 25% moisture. Total A75 ml=total fermentor volume in ml.

Figure 7:
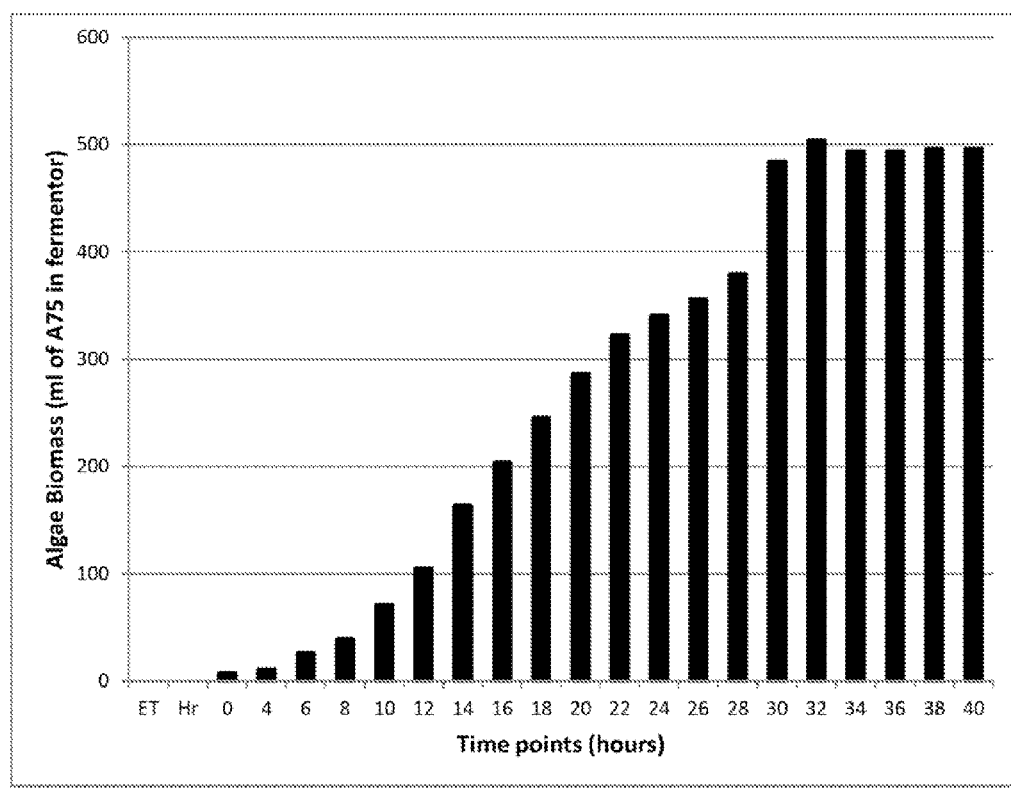
FIG. 7 is a graph depicting the biomass of a *Chlorella* species culture, at the indicated time points, during the course of a heterotrophic cultivation according to an embodiment of the present disclosure.

FIG. 7 is a graph depicting the total A75 in ml values as indicated in Table 1. The microalgae biomass in ml (milliliters) is shown at each time point, as indicated. This graph shows the total volume of the A75. Each sample was first propagated under heterotrophic growth conditions, without the introduction of oxygen, for about 10 hours. After the about 10 hours, oxygen was introduced into each of the microalgae propagations and the oxygen was introduced throughout the remainder of the propagation. Accordingly, the 0 hour time point in Table 1 is measured from the end of the 10 hour cultivation period, without introduced oxygen, as described above. Thus, the 0 hour time point is at about 10 hours after the onset of the heterotrophic growth conditions. As indicated in FIG. 7, at about the 28 hour time point to about the 30 hour time point, the increase in microalgae biomass slowed and/or plateaued.

TABLE 1

Chlorella Propagations Averaged - Biomass

| ET Hr | Vol liter | Sugar grams | Ammonia ml* | pH | CT mm | Temp (° F.) | Change A75 Height (mm) | Total A75 ml |
|---|---|---|---|---|---|---|---|---|
| 0 | 12 | 250 | | 6.5 | 0.25 | 86 | | 7.41 |
| 4 | 12.25 | 25 | 60 | 5.6-6.8 | 0.35 | 86 | 0.1 | 10.59 |
| 6 | 12.5 | 25 | 36 | 6-6.6 | 0.85 | 86 | 0.5 | 26.23 |
| 8 | 12.75 | 30 | 80 | 5.7-6.8 | 1.24 | 87 | 0.39 | 39.04 |
| 10 | 13 | 35 | | | 2.2 | 88 | 0.96 | 70.62 |
| 12 | 13.25 | 35 | 100 | 5.4-6.9 | 3.2 | 88 | 1 | 104.69 |
| 14 | 13.5 | 35 | | | 4.9 | 88 | 1.7 | 163.33 |
| 16 | 13.75 | 35 | 80 | 5.5-6.6 | 6 | 89 | 1.1 | 203.70 |
| 18 | 14 | 35 | 80 | 5.7-6.5 | 7.1 | 89 | 1.1 | 245.43 |
| 20 | 14.5 | 35 | 48 | 5.8-6.6 | 8 | 88 | 0.9 | 286.42 |
| 22 | 15 | 35 | 48 | 5.8-6.4 | 8.7 | 88 | 0.7 | 322.22 |
| 24 | 15.5 | 35 | 48 | 5.9-6.4 | 8.9 | 87 | 0.2 | 340.62 |
| 26 | 16 | | | | 9 | 88 | 0.1 | 355.56 |
| 28 | 16.5 | | | 5.9-6.5 | 9.3 | 86 | 0.3 | 378.89 |
| 30 | 20 | | | 5.7-6.3 | 9.8 | 89 | 0.5 | 483.95 |
| 32 | 20 | | | 5.5-6.2 | 10.2 | 90 | 0.4 | 503.70 |
| 34 | 20 | | | 5.0-5.9 | 10 | 89 | -0.2 | 493.83 |
| 36 | 20 | | | 5.0-5.8 | 10 | 90 | 0 | 493.83 |
| 38 | 20.5 | | | 5.0-5.5 | 9.8 | 89 | -0.2 | 496.05 |
| 40 | 20.5 | | | 4.8-5.4 | 9.8 | 89 | 0 | 496.05 |

*diluted solution to give 100 g/L
13.5 mm = 0.5 ml
0.037037 A75/CT mm

Example 3

Ten (10) propagations of *Chlorella* were prepared to optimize the production of protein. Table 2 depicts the volume in liters of the inoculated culture media at various time points (e.g., 0 hours, 4 hours, 6 hours, etc.) of the 10 propagations. The average amount of sugar (in grams) introduced into the inoculated culture media at various time points is also shown. The sugar, as stated above, was introduced as a nutrient source for the microalgae. The amount of ammonia (in ml, diluted in solution to give 100 g/L) introduced into the inoculated culture media at various time points is also shown. The ammonia, as stated above, was introduced to adjust the pH of the inoculated culture media.

With continued reference to Table 2, an ending pH (i.e., after ammonia was used to adjust the pH) is depicted. The "CT mm" column indicates the height of the microalgae mass inside a 15 ml centrifuge tube after centrifugation of the sample. Each sample had a volume of about 15 ml, and was centrifuged, or spun, for about 10 minutes at about 5000 rpm. The maximum temperature in Fahrenheit at specified time points is also indicated. The final column represents a conversion from height to volume of the microalgae mass collected in the bottom of the centrifuge tubes, as described in Example 2.

TABLE 2

Chlorella Propagations Averaged - Protein

| ET Hr | Vol liter | Sugar grams | Ammonia ml* | pH max | CT mm | Temp max | Total A75 ml |
|---|---|---|---|---|---|---|---|
| 0 | 12 | 250 | | 6.5 | 0.15 | 86 | 4.44 |
| 4 | 12.25 | 25 | 80 | 6.9 | 0.15 | 86 | 4.54 |
| 6 | 12.5 | 25 | 80 | 7.2 | 0.2 | 86 | 6.17 |
| 8 | 12.75 | 30 | 80 | 7.4 | 0.2 | 90 | 6.30 |
| 10 | 13 | 35 | | 7.8 | 0.5 | 90 | 16.05 |
| 12 | 13.25 | 35 | 80 | 8 | 0.8 | 92 | 26.17 |
| 14 | 13.5 | 35 | 80 | 8 | 1.2 | 92 | 39.99 |
| 16 | 13.75 | 35 | 80 | 8 | 2.2 | 95 | 74.69 |
| 18 | 14 | 35 | 80 | 8 | 4.2 | 95 | 145.19 |
| 20 | 14.5 | 35 | 80 | 8.4 | 5.1 | 95 | 182.59 |
| 22 | 15 | 35 | 80 | 8.4 | 6.4 | 95 | 237.04 |
| 24 | 15.5 | 35 | 90 | 8.4 | 7.3 | 95 | 279.38 |
| 26 | 16 | | 90 | 8.6 | 8.1 | 95 | 319.99 |
| 28 | 16.5 | | | 8.6 | 8.8 | 95 | 358.52 |
| 30 | 20 | | | 8.5 | 9.2 | 95 | 454.32 |
| 32 | 20 | | | 8.4 | 9.8 | 95 | 483.95 |
| 34 | 20 | | | 8.2 | 9.9 | 92 | 488.89 |
| 36 | 20 | | | 8.2 | 9.9 | 92 | 488.89 |
| 38 | 20.5 | | | 8.2 | 9.8 | 90 | 496.05 |
| 40 | 20.5 | | | 8 | 9.8 | 90 | 496.05 |

*diluted solution to give 100 g/L
13.5 mm = 0.5 ml
0.037037 A75/CT mm

Figure 8:
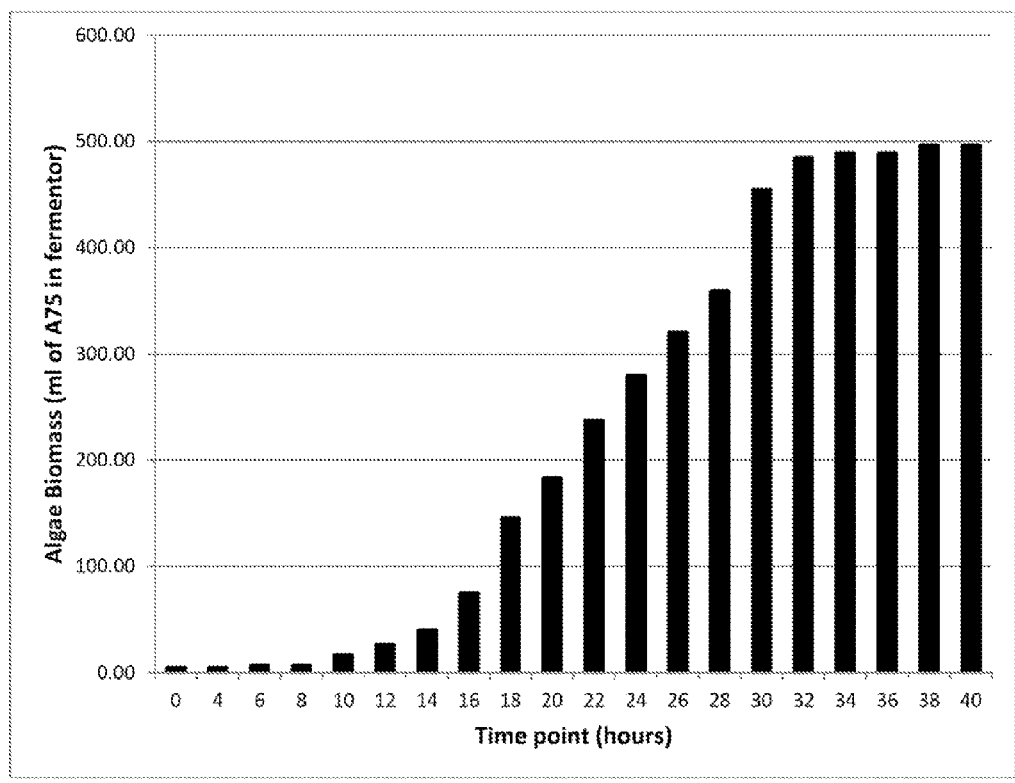
FIG. 8 is a graph depicting the biomass of a *Chlorella* species culture, at the indicated time points, during the course of another heterotrophic cultivation according to an embodiment of the present disclosure.

FIG. 8 is a graph depicting the total A75 in ml values as indicated in Table 2. The microalgae biomass in ml (milliliters) is shown at each time point, as indicated. This graph shows the total volume of the A75. Each sample was first propagated under heterotrophic growth conditions, without the introduction of oxygen, for about 10 hours. After the about 10 hours, oxygen was introduced into each of the microalgae propagations and the oxygen was introduced throughout the remainder of the propagation. Accordingly, the 0 hour time point in Table 1 is measured from the end of the 10 hour cultivation period, without introduced oxygen, as described above. Thus, the 0 hour time point is at about 10 hours after the onset of the heterotrophic growth conditions. As indicated in FIG. 8, at about the 28 hour time point to about the 30 hour time point, the increase in microalgae biomass slowed and/or plateaued.

As will be understood by one of ordinary skill in the art, each embodiment disclosed herein can comprise, consist essentially of, or consist of its particular stated element, step, ingredient, or component. As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components, and to those that do not materially affect the embodiment.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e., denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The applicants expect skilled artisans to employ such variations as appropriate, and the applicants intend for the various embodiments of the disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the present disclosure are illustrative of the principles of the present disclosure. Other modifications that may be employed are within the scope of the disclosure. Thus, by way of example, but not of limitation, alternative configurations of the present disclosure may be utilized in accordance with the teachings herein. Accordingly, the present disclosure is not limited to that precisely as shown and described.

The particulars shown herein are by way of example and for purposes of illustrative discussion of the preferred embodiments of the present disclosure only and are presented in the cause of providing what is believed to be the most useful and readily understood description of the principles and conceptual aspects of various embodiments of the disclosure.

Definitions and explanations used in the present disclosure are meant and intended to be controlling in any future construction unless clearly and unambiguously modified in the following examples or when application of the meaning renders any construction meaningless or essentially meaningless in cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

It will be apparent to those having skill in the art that many changes may be made to the details of the above-described embodiments without departing from the underlying principles of the invention. The scope of the present invention should, therefore, be determined only by the following claims.

The invention claimed is:

1. A method of inducing production of increased microalgae biomass, the method comprising:
    inoculating a culture media with microalgae, wherein the microalgae is selected from at least one of *Chlorella* species and *Nannochloropsis* species;
    cultivating the microalgae under heterotrophic growth conditions; and
    delivering oxygen gas into the inoculated culture media, wherein the oxygen gas comprises between about 80% and 100% oxygen.

2. The method of claim 1, wherein the microalgae biomass increases at a greater rate than the microalgae under autotrophic growth conditions.

3. The method of claim 1, wherein cultivating the microalgae under heterotrophic growth conditions comprises reducing exposure of the inoculated culture media to light.

4. The method of claim 1, wherein cultivating the microalgae under heterotrophic growth conditions comprises subjecting the inoculated culture media to a substantially dark environment.

5. The method of claim 1, wherein the oxygen gas is delivered into the inoculated culture media at a rate of between about 0.1 L/minute to about 2.5 L/minute for each 10 L volume of inoculated culture media.

6. The method of claim 1, wherein the oxygen gas is delivered into the inoculated culture media via a gas line such that the oxygen gas diffuses through the inoculated culture media.

7. The method of claim 1, wherein the microalgae is selected from at least one of *Chlorella fusca*, *Chlorella protothecoides*, *Chlorella pyrenoidosa*, *Chlorella kessleri*, *Chlorella vulgaris*, *Chlorella saccharophila*, *Chlorella sorokiniana*, and *Chlorella ellipsoidea*.

8. The method of claim 1, further comprising:
cultivating the microalgae under autotrophic growth conditions prior to inoculating the culture media with the microalgae.

9. The method of claim 1, wherein the culture media comprises a carbon source.

10. The method of claim 9, wherein the carbon source is selected from at least one of dextrose, glucose, fructose, sucrose, galactose, xylose, mannose, rhamnose, N-acetylglucosamine, glycerol, floridoside, glucuronic acid, corn starch, depolymerized cellulosic material, sugar cane, sugar beet, lactose, milk whey, and molasses.

11. The method of claim 9, wherein the culture media further comprises at least one of a fat source, a nitrogen source, a phosphorus source, a coenzyme, and a coenzyme factor.

12. The method of claim 1, further comprising:
maintaining a pH of the inoculated culture media between about a pH of 5.5 and about a pH of 6.2.

13. The method of claim 1, wherein the oxygen gas is delivered at a rate of about 1.0 L/minute per 10 L of inoculated culture media.

14. The method of claim 1, wherein the oxygen gas is delivered into the inoculated culture media at a rate of between about 0.1 L/minute to about 2.5 L/minute per 10 L of inoculated culture media.

15. The method of claim 1, further comprising:
maintaining a temperature of the inoculated culture media between about 21° C. and about 28° C.

16. The method of claim 1, wherein the oxygen gas comprises between about 85% and 100% oxygen.

17. A method of inducing production of increased microalgae biomass, the method comprising:
inoculating a culture media with microalgae, wherein the microalgae is selected from at least one of *Chlorella* species and *Nannochloropsis* species;
cultivating the microalgae under heterotrophic growth conditions;
delivering oxygen gas into the inoculated culture media, wherein the oxygen gas comprises between about 80% and 100% oxygen;
maintaining a pH of the inoculated culture media between about a pH of 5.5 and about a pH of 6.2; and
maintaining a temperature of the inoculated culture media between about 21° C. and about 28° C.

18. The method of claim 17, wherein the oxygen gas comprises between about 85% and 100% oxygen.

19. The method of claim 17, wherein the oxygen gas is delivered into the inoculated culture media at a rate of between about 0.1 L/minute to about 2.5 L/minute per 10 L of inoculated culture media.

20. The method of claim 17, wherein the oxygen gas is delivered into the inoculated culture media at a rate of about 1.0 L/minute per 10 L of inoculated culture media.

21. The method of claim 1, further comprising:
maintaining a pH of the inoculated culture media between about a pH of 4.0 and about a pH of 9.5.

22. The method of claim 1, further comprising:
maintaining a temperature of the inoculated culture media between about 15° C. and about 40° C.

* * * * *